(12) United States Patent
Sigl et al.

(10) Patent No.: US 7,642,383 B2
(45) Date of Patent: Jan. 5, 2010

(54) PROCESS FOR PREPARING ALKYLAMINES BY REACTING OLEFINS WITH AMMONIA

(75) Inventors: Marcus Sigl, Mannheim (DE); Ralf Böhling, Lorsch (DE); Peter Zehner, Weisenheim am Berg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/091,618

(22) PCT Filed: Oct. 20, 2006

(86) PCT No.: PCT/EP2006/067602

§ 371 (c)(1),
(2), (4) Date: Apr. 25, 2008

(87) PCT Pub. No.: WO2007/048753

PCT Pub. Date: May 3, 2007

(65) Prior Publication Data

US 2008/0319230 A1    Dec. 25, 2008

(30) Foreign Application Priority Data

Oct. 25, 2005   (DE) ..................... 10 2005 051 044

(51) Int. Cl.
*C07C 209/60* (2006.01)

(52) U.S. Cl. .................................................. 564/485

(58) Field of Classification Search .................. 564/485
See application file for complete search history.

(56) References Cited

U.S. PATENT DOCUMENTS

| 4,929,758 | A | 5/1990 | Taglieber et al. |
| 5,763,668 | A | 6/1998 | Dingerdissen et al. |
| 6,350,914 | B1 | 2/2002 | Eller et al. |
| 6,809,222 | B1 | 10/2004 | Pasek et al. |

FOREIGN PATENT DOCUMENTS

| EP | A 132 736 | 7/1984 |
| EP | A 721 934 | 7/1996 |
| EP | A 752 409 | 8/1997 |
| EP | A 822 179 | 2/1998 |
| WO | WO 01/85667 | 11/2001 |

*Primary Examiner*—Brian J Davis
(74) *Attorney, Agent, or Firm*—Connolly Bove Lodge & Hutz LLP

(57) ABSTRACT

A process for preparing alkylamines by reacting olefins with ammonia under hydroaminating conditions over a calcined zeolitic catalyst in an adiabatically operated reactor unit, wherein the reaction mixture comprising the starting olefin, ammonia and the corresponding alkylamine is taken off at one or more points and brought into indirect thermal contact with the reaction mixture at one or more points in the reactor unit having in each case a lower concentration of alkylamine compared to the point from which the reaction mixture was taken off, is proposed.

20 Claims, No Drawings

PROCESS FOR PREPARING ALKYLAMINES BY REACTING OLEFINS WITH AMMONIA

The present application is a National Phase of PCT Application No. PCT/EP2006/067602, filed Oct. 20, 2006, which claims priority to German Application 102005051044.2, filed Oct. 25, 2005, the entire disclosures of which are incorporated herein by reference.

The invention relates to a process for preparing alkylamines by reacting olefins with ammonia under hydroaminating conditions over a calcined zeolitic catalyst in an adiabatically operated reactor unit.

The addition of ammonia onto olefins is exothermic; low temperatures are therefore advantageous for shifting the equilibrium in the direction of the desired alkylamine product. However, the reaction rates are low at low temperatures. There has therefore been a search for catalysts which ensure a satisfactory reaction rate even at relatively low temperatures. Since not only low temperatures but also high pressures are advantageous for the position of the equilibrium, the reaction is generally carried out under superatmospheric pressure, frequently in the range from 40 to 500 bar, preferably from 150 to 300 bar. The position of the temperature optimum for conversion and selectivity is dependent on the nature of the olefin and the catalyst used and is usually in the range from 230 to 320° C. However, even at the temperature optimum and under superatmospheric pressure, a single pass through the reactor gives conversions of only from 5 to 20%, frequently from 10 to 15%.

Processes for preparing alkylamines by reacting olefins with ammonia over calcined zeolitic catalysts are described, for example, in EP-A 132 736, EP-A 752 409, EP-A 822 179 or U.S. Pat. No. 6,809,222.

It was thus an object of the invention to provide a process by means of which the yield based on olefin can be increased in a technically simple manner. In particular, it should be possible to modify existing high-pressure reactors in a simple manner without the internal volume of the apparatus through which the reaction mixture flows being reduced appreciably, i.e. by up to a maximum of 10%, and in particular without facilities for an external coolant being necessary.

The achievement of this object starts out from a process for preparing alkylamines by reacting olefins with ammonia under hydroaminating conditions over a calcined zeolitic catalyst in an adiabatically operated reactor unit.

In the process of the invention, the reaction mixture comprising the starting olefin, ammonia and the corresponding alkylamine is taken off at one or more points and brought into indirect thermal contact with the reaction mixture at one or more points in the reactor unit having in each case a lower concentration of alkylamine compared to the point or points from which the reaction mixture was taken off.

It has been found that it is possible to increase the conversion of olefin in a process for preparing alkylamines under adiabatic reaction conditions by utilizing the reaction mixture from one or more suitable points in the reactor unit for cooling the reaction gas mixture at one or more suitable points by indirect heat exchange, always utilizing a reaction mixture having a lower concentration of alkylamine to cool a reaction mixture having a higher concentration of alkylamine by indirect heat exchange.

Although the temperature difference between feed stream and the product mixture taken off in this specific way of carrying out the process corresponds to the adiabatic temperature increase caused by the heat of reaction, the reactor outlet temperature is significantly lower than the maximum reaction temperature.

In a particularly advantageous process variant, the reaction mixture comprising the starting olefin, ammonia and the corresponding alkylamine is diverted in the middle of its flow path through the reactor unit and put into indirect countercurrent thermal contact with the reaction mixture conveyed up to the middle of the flow path in the reactor. In this way of carrying put the process, the highest temperature in the reactor is reached not at the outlet for the reaction mixture but in the middle of its flow path through the reactor.

The reaction mixture obtained from a first reaction unit can advantageously be introduced into one or more further reaction units which are configured analogously to the first reaction unit. The individual reactor units connected in series can be arranged in a single pressure-resistant outer shell.

As a result of two or more reactor units being provided, the single reactor unit can be designed with a shorter length and a correspondingly lower pressure drop.

To carry out the reaction of the olefin with ammonia, ammonia is firstly mixed in a known manner with olefin in a molar ratio of from 1:1 to 10:1, preferably from 1:1 to 5:1, and the reaction is carried out in a fixed-bed reactor or a fluidized-bed reactor at a pressure of from 40 to 500 bar, preferably from 150 to 300 bar, and a temperature of from 80 to 400° C., preferably from 230 to 320° C., in the gas phase or in the supercritical state.

In one embodiment of the process, ammonia mixed with the olefin in a molar ratio of from 1:1 to 5:1 is fed to a fixed-bed reactor which comprises the calcined zeolitic catalyst and reacted in a single-phase state at a pressure of from 40 to 500 bar, preferably from 150 to 310 bar, in particular from 200 to 280 bar, and a temperature of from 200 to 350° C., preferably from 230 to 320° C.

As olefins, it is possible to use, in particular, linear or branched aliphatic $C_3$-$C_5$-olefins. Preferred olefinic starting materials are butene and in particular isobutene. Accordingly, the particularly preferred hydroamination product, obtained from ammonia and isobutene, is tert-butylamine.

Calcined zeolitic catalysts are used in the process of the invention. This means that the active composition of the catalyst is made up of zeolites. Zeolitic catalysts usually further comprise binders which are necessary for producing the shaped catalyst bodies. In the production of shaped catalyst bodies from corresponding molding compositions, the shaped bodies are usually dried and then calcined.

This generally requires a temperature of more than 400° C. for the binder material to harden. The maximum temperature is restricted by the stability of the zeolite which loses its crystallinity at temperatures above 550° C. The calcination is carried out industrially in a rotary tube at a temperature in the range from 400 to 550° C. and a residence time of from 1 to 4 hours. In the laboratory, it is usually carried out in a furnace at a temperature of from 480 to 520° C. for a period of from 2 to 16 hours.

Suitable catalysts for the hydroamination of olefins by means of ammonia and/or a primary amine are zeolites, in particular faujasites such as X-, Y- and USY-zeolite, erionite, chabazite, mordenite, offretite, clinoptiolite, pentasils such as ZSM-5 and ZBM-10, ZSM-11, ZSM-12, MCM-22, MCM41, MCM48, MCM49, MCM-56, EMT, SSZ-26, SSZ-33, SSZ-37, CIT-1, PSH-3, NU-85, beta and the boron-comprising forms, for example ZBM-11, H-boron-ZSM-5, H-boron-beta, H-boron-ZSM-11 and also the gallium- or titanium-comprising forms. They have a large number of catalytically active sites, combined with a large surface area.

The zeolites described differ in terms of type and in the way they have been after-treated after their preparation (for example thermal treatment, dealumination, acid treatment, metal ion exchange, etc.).

Examples of suitable zeolites may be found in U.S. Pat. No. 4,375,002, U.S. Pat. No. 4,536,602, EP-A 305 564, EP-A 101 921 and DE-A 42 06 992.

The zeolites known from EP-A 133 938, EP-A 431 451 and EP-A 132 736, which are boron silicate, gallium silicate, aluminosilicate and iron silicate zeolites which may optionally be doped as described with alkali metals, alkaline earth metals and transition metals, are also suitable.

Furthermore, the beta-zeolites known from CA-A 2 092 964, for example, which are defined as crystalline aluminosilicates having a particular composition and a pore size of more than 5 Å, are also suitable.

Preference is given to using metal- or halogen-modified beta-zeolites as described, for example, in DE-A 195 30 177.

Zeolite catalysts of the pentasil type having an $SiO_2/Al_2O_3$ molar ratio of greater than or equal to 10, as disclosed in EP-A 132 736, are also particularly suitable.

The aluminum phosphates and silicoaluminophosphates include the crystalline systems having zeolite structures or zeolite-like structures, for example SAPO-37, $AlPO_4$-5, SAPO-5 as described in DE-A 196 01 409, and also amorphous systems as described, for example, in DE-A 44 31 093. They generally have the formula $Al_2O_3 * P_2O_5 * xSiO_2$.

The catalysts can be used in the form of powder or preferably as shaped bodies such as spheres, extrudates, pellets or crushed material. To carry out shaping, it is possible to add from 10 to 60% by weight (based on the composition to be shaped) of binders. Suitable binders are various aluminum oxides, preferably boehmite, amorphous aluminosilicates having a molar $SiO_2/Al_2O_3$ ratio of from 25:75 to 95:5, silicon dioxide, preferably finely divided $SiO_2$, for example silica sols, mixtures of finely divided $SiO_2$ and finely divided $Al_2O_3$, finely divided $TiO_2$ and clays.

After shaping, the extrudates or pressed bodies are advantageously dried at from 80 to 150° C. for from 1 to 16 hours and calcined at from 300 to 500° C. for from 1 to 16 hours, with calcinations also being able, like activation, to be carried out directly in the hydroamination reactor.

The catalysts are generally used in the H form. However, various modifications can also be carried out on the catalysts to increase the selectivity, the operating life and the number of possible catalyst regenerations.

One modification of the catalysts comprises doping the unshaped catalysts with alkali metals such as Na and K, alkaline earth metals such as Ca and Mg, transition metals such as Mn, Fe, Mo, Cu, Zn and Cr, noble metals and/or rare earth metals such as La, Ce and Y.

In an advantageous embodiment of the catalysts, the shaped and calcined catalysts are placed in a flow tube and, for example, a halide, an acetate, an oxalate, a citrate or a nitrate of the above-described metals in dissolved form is passed over them at from 20 to 100° C. Such an ion exchange can, for example, be carried out on the hydrogen, ammonium and alkali metal form of the catalysts.

Another possible way of applying the metals to the catalysts is to impregnate the zeolitic material with, for example, a halide, acetate, oxalate, citrate, nitrate or oxide of the above-described metals in aqueous or alcoholic solution.

Both ion exchange and impregnation can be followed by drying and if desired another calcination. An after-treatment of the metal-doped catalysts with hydrogen and/or water vapor can be advantageous.

A further possible way of modifying the catalyst is to subject the heterogeneous catalytic material, shaped or unshaped, to a treatment with acids such as hydrochloric acid (HCl), hydrofluoric acid (HF), phosphoric acid ($H_3PO_4$), sulfuric acid ($H_2SO_4$), oxalic acid ($HO_2C—CO_2H$) or mixtures thereof.

A particular embodiment comprises treating the catalyst powder before shaping with hydrofluoric acid (from 0.001 to 2 molar, preferably from 0.05 to 0.5 molar) under reflux for from 1 to 3 hours. After filtration and washing, the catalyst powder is generally dried at from 100 to 160° C. and calcined at from 400 to 550° C.

A further particular embodiment comprises an HCl treatment of the heterogeneous catalysts after shaping with binders. Here, the heterogeneous catalyst is generally treated with a 3-25% strength, in particular a 12-20% strength, hydrochloric acid at temperatures of from 60 to 80° C. for from 1 to 3 hours, subsequently washed, dried at from 100 to 160° C. and calcined at from 400 to 550° C.

Another possible way of modifying the catalyst is exchange with ammonium salts, for example with $NH_4Cl$, or with monoamines, diamines or polyamines. Here, the heterogeneous catalyst shaped with a binder is generally exchanged continuously with 10-25% strength, preferably about 20% strength, $NH_4Cl$ solution at a heterogeneous catalyst/ammonium chloride solution weight ratio of 1:15 at from 60 to 80° C. for 2 hours and then dried at from 100 to 120° C.

A further modification which can be carried out on aluminum-comprising catalysts is dealumination in which part of the aluminum atoms are replaced by silicon or the aluminum content of the catalysts is reduced by, for example, hydrothermal treatment. Hydrothermal dealumination is advantageously followed by extraction with acids or complexing agents to remove nonlattice aluminum formed. The replacement of aluminum by silicon can, for example, be effected by means of $(NH_4)_2SiF_6$ or $SiCl_4$. Examples of dealuminations of Y zeolites may be found in Corma et al., Stud. Surf. Sci. Catal. 37 (1987), pages 495 to 503.

The catalysts can be used as extrudates having diameters of, for example, from 1 to 4 mm or as pellets having diameters of, for example, from 3 to 5 mm for the hydroamination of the olefins.

The reactor unit is generally a reactor, preferably a shaft apparatus, which is provided with internals. These internals are configured so that relatively cold and relatively hot reaction mixture can be conveyed past one another in indirect thermal contact in countercurrent.

The internals can, for example, be configured as bundles of tubes or as separation plates in the shaft apparatus.

It is particularly advantageous to design the internals so that the heat transport path for the reaction mixture is from 3 to 15 mm, in particular from 5 to 10 mm.

Here, the heat transport path in the structural variant of a bundle of tubes corresponds to the internal diameter of the tubes and that in the variant with separation plates corresponds to the distance between two successive separation plates.

The invention is illustrated below by means of an example.

In a simulation, the maximum achievable conversion of isobutene in a process for preparing tert-butylamines from isobutene and ammonia over a zeolitic catalyst at a reaction pressure of 280 bar and under adiabatic reaction conditions without cooling of the reaction mixture (for comparison) and with cooling of the reaction mixture by diversion of the reaction mixture in the middle of the flow path of the reaction mixture through the reactor and indirect heat exchange with the reaction medium circulating through the reactor in the first half of the flow path (corresponding to the invention) were compared.

The input temperatures for the feed stream were in each case conversion-optimized, i.e. the input temperatures at which the maximum conversion could be achieved were calculated in each case. These were an inlet temperature of 253° C. for the comparative process and an inlet temperature of 245° C. for the process according to the invention. In the comparative process, an isobutene conversion of 15.8% was achieved, compared to a conversion of 16.8% in the case of the process according to the invention.

The invention claimed is:

1. A process for preparing alkylamines by reacting olefins with ammonia under hydroaminating conditions over a calcined zeolitic catalyst in an adiabatically operated reactor unit, wherein the reaction mixture comprising the staffing olefin, ammonia and the corresponding alkylamine is taken off at one or more points and brought into indirect thermal contact with the reaction mixture at one or more points in the reactor unit having in each case a lower concentration of alkylamine compared to the point from which the reaction mixture was taken off.

2. A process for preparing alkylamines by reacting olefins with ammonia under hydroaminating conditions over a calcined zeolitic catalyst in an adiabatically operated reactor unit, wherein the reaction mixture comprising the staffing olefin, ammonia and the corresponding alkylamine is diverted in the middle of its flow path through the reactor unit and put in to indirect countercurrent thermal contact with the reaction mixture conveyed up to the middle of the flow path in the reactor unit.

3. The process according to claim 1, wherein a plurality of reactor units are connected.

4. The process according to claim 1, wherein the olefins are selected from among $C_3$-$C_5$-olefins.

5. The process according to claim 4, wherein the olefin is isobutene.

6. The process according to claim 1, wherein the reactor unit is a shaft apparatus provided with internals.

7. The process according to claim 6, wherein the internals are separation plates or a bundle of tubes.

8. The process according to claim 6, wherein the heat transport path in the internals is from 3 to 15 mm.

9. The process according to claim 8, wherein the heat transport path is from 5 to 10 mm.

10. The process according to claim 8, wherein the heat transport path corresponds to the internal diameter of the tubes of the bundle of tubes or to the distance between two successive separation plates.

11. The process according to claim 2, wherein a plurality of reactor units are connected.

12. The process according to claim 2, wherein the olefins are selected from among $C_3$-$C_5$-olefins.

13. The process according to claim 3, wherein the olefins are selected from among $C_3$-$C_5$-olefins.

14. The process according to claim 2, wherein the reactor unit is a shaft apparatus provided with internals.

15. The process according to claim 3, wherein the reactor unit is a shaft apparatus provided with internals.

16. The process according to claim 4, wherein the reactor unit is a shaft apparatus provided with internals.

17. The process according to claim 5, wherein the reactor unit is a shaft apparatus provided with internals.

18. The process according to claim 7, wherein the heat transport path in the internals is from 3 to 15 mm.

19. The process according to claim 9, wherein the heat transport path corresponds to the internal diameter of the tubes of the bundle of tubes or to the distance between two successive separation plates.

20. The process according to claim 2, wherein the olefin is isobutene.

* * * * *